US010766138B2

(12) United States Patent
Perplies et al.

(10) Patent No.: US 10,766,138 B2
(45) Date of Patent: Sep. 8, 2020

(54) STAND DEVICE RESPONSIVE TO FORCE OR MOVEMENT, CONTROL DEVICE, AND METHOD FOR POSITIONING THE STAND DEVICE

(71) Applicant: Ondal Medical Systems GmbH, Hünfeld (DE)

(72) Inventors: Stefan Perplies, Hünfeld (DE); Kai Volkenand, Hünfeld (DE)

(73) Assignee: Ondal Medical Systems GmbH, Hünfeld (DE)

( * ) Notice: Subject to any disclaimer, the term of this patent is extended or adjusted under 35 U.S.C. 154(b) by 404 days.

(21) Appl. No.: 15/504,249

(22) PCT Filed: Jul. 9, 2015

(86) PCT No.: PCT/EP2015/001398
§ 371 (c)(1),
(2) Date: Jul. 27, 2017

(87) PCT Pub. No.: WO2016/026547
PCT Pub. Date: Feb. 25, 2016

(65) Prior Publication Data
US 2017/0341232 A1    Nov. 30, 2017

(30) Foreign Application Priority Data

Aug. 18, 2014   (EP) ..................................... 14002864

(51) Int. Cl.
*B25J 9/16* (2006.01)
*A61B 90/50* (2016.01)
(Continued)

(52) U.S. Cl.
CPC ............. *B25J 9/1674* (2013.01); *A61B 90/50* (2016.02); *A61G 12/002* (2013.01);
(Continued)

(58) Field of Classification Search
CPC .... B25J 9/1674; B25J 19/0004; B25J 9/1694; A61B 90/50; A61B 2090/064;
(Continued)

(56) References Cited

U.S. PATENT DOCUMENTS 9,367,061 B2 *  6/2016  Miller .................. G05B 19/042
2005/0075739 A1 *  4/2005  Nishizawa ............. B25J 9/1065
                                                    700/65
(Continued)

FOREIGN PATENT DOCUMENTS

EP        2 455 053 B1    9/2013
JP        2009-291363 A   12/2009

*Primary Examiner* — Jason Holloway
(74) *Attorney, Agent, or Firm* — Seed Intellectual Property Law Group LLP (57) ABSTRACT

A stand device for arranging in an operating room and for locally moving a medical device can incorporate a braking device having at least one brake to adjust a degree of freedom of movement of the medical device or a support system holding the device, wherein the stand device can further comprise a control device connected to the braking device to evaluate an external force acting on the stand device or a movement caused by the external force and configured to control the braking device and to adjust the degree of freedom of movement. The medical device can be moved without operating a switch/pushbutton. Furthermore, the disclosure relates to control devices and a methods for positioning the medical device.

10 Claims, 3 Drawing Sheets (51) Int. Cl.
    *A61G 13/10*     (2006.01)
    *A61G 12/00*     (2006.01)
    *B25J 19/00*     (2006.01)
    *A61B 90/00*     (2016.01)

(52) U.S. Cl.
    CPC .......... *A61G 13/107* (2013.01); *B25J 9/1694* (2013.01); *B25J 19/0004* (2013.01); *A61B 2090/064* (2016.02); *A61B 2090/508* (2016.02); *A61G 12/004* (2013.01); *A61G 12/005* (2013.01); *A61G 12/007* (2013.01); *A61G 2203/32* (2013.01); *A61G 2203/34* (2013.01); *A61G 2203/36* (2013.01); *A61G 2203/38* (2013.01); *Y10S 901/09* (2013.01)

(58) Field of Classification Search
    CPC ............ A61B 2090/508; A61G 12/002; A61G 13/107; A61G 12/007; A61G 12/005; A61G 12/004; A61G 2203/38; A61G 2203/34; A61G 2203/32; A61G 2203/36; Y10S 901/09
    See application file for complete search history.

(56) References Cited

U.S. PATENT DOCUMENTS

| | | | |
|---|---|---|---|
| 2005/0166413 A1* | 8/2005 | Crampton | B25J 13/088 33/503 |
| 2005/0222714 A1* | 10/2005 | Nihei | G05B 19/423 700/264 |
| 2013/0221183 A1* | 8/2013 | Volkenand | A61G 12/004 248/550 |
| 2013/0338430 A1* | 12/2013 | Volkenand | A61G 12/004 600/28 |
| 2015/0290809 A1* | 10/2015 | Nakagawa | B25J 9/1676 700/258 |
| 2016/0052128 A1* | 2/2016 | Zimmermann | B25J 9/0081 700/261 |
| 2016/0059407 A1* | 3/2016 | Sonoda | B25J 9/0081 700/260 |
| 2017/0095932 A1* | 4/2017 | Murakami | B25J 9/0081 |
| 2017/0254709 A1* | 9/2017 | Lauzier | B25J 9/0081 |
| 2018/0066794 A1* | 3/2018 | Okuda | A61B 90/60 |
| 2018/0296285 A1* | 10/2018 | Simi | A61B 17/062 |

* cited by examiner

STAND DEVICE RESPONSIVE TO FORCE OR MOVEMENT, CONTROL DEVICE, AND METHOD FOR POSITIONING THE STAND DEVICE

BACKGROUND

Technical Field

The present disclosure relates to a stand device for arranging in an operating room and for locally moving a medical device, comprising a braking device having at least one brake that is configured to adjust a degree of freedom of movement of the medical device. In particular, the present disclosure relates to a stand device having individual features of claim 1 and a control device for it, as well as a method for positioning a medical device having individual features of the corresponding independent method claim.

Description of the Related Art

Stands—in particular, ceiling stands such as ceiling supply units, monitor supports, or so-called spring arms or central axes, usually have one or more carriers/support arms that are arranged rigidly or so that they are adjustable in height with respect to a vertical position, by means of which an attached medical device may be moved and positioned, e.g., in an operating room—in particular, also in an intensive care unit. The stands usually have supply units and/or, for example, medical-electrical bedside terminals mounted on them that are, for example, supplied with the required media during an operation. The carriers define a radius of action of the medical device in which the medical device can be positioned. The carriers may usually be rotated around at least one rotatable connection—in particular, a swivel joint. The carriers are also optionally arranged in a height-adjustable manner and/or in a manner in which they can be pivoted vertically around an at least approximately horizontal axis. The vertical adjustability is an advantageous function, particularly for ceiling stands.

It must be possible to firmly arrange the stand or the respective medical device in specific positions with regard to a particular operation, a particular patient, or particular supply lines. Therefore, the stands usually have a braking device or some kind of blocking function that can ensure that the medical device remains in a specified position, even if people or objects bump into it.

On the other hand, it should also be possible to reposition the stand or the respective medical device in a simple way, be it during an operation or between two consecutive operations, or for different patients or patient tables. Ideally, it should be possible to move the stand or the medical device to a certain position intuitively and without much effort, even if it has a variety of support arms. Intuitive operation/positioning of the medical device is also desirable in low-light conditions or in stressful situations.

Because the stands or medical devices may be devices having significant mass, the medical device is also usually moved or repositioned with at least the help of motorized actuators—in particular, with respect to up and down movement. It should also be possible in many cases to slow down a rotational movement of individual carriers, be it an absolute rotational movement or a rotational movement relative to another carrier, automatically or using a motor. Doing so may, for example, prevent a carrier from rotating around more than one specified angle relative to another carrier. The automatic braking also has the advantage that the individual carrier or medical device does not need to be guided manually throughout the entire movement. Motorized or automatic braking may, for example, be done in a swivel joint or a bearing. The braking effect of, for example, a frictional brake can, for example, be set or adjusted.

To reposition the medical device, the operator must usually release a respective braking device by first manually pressing a control button or pushbutton—in particular, a control button arranged on the carrier, on a control panel, or a standard rail of a supply unit. The medical device or the carrier can then be moved manually or with a motor. In other words, repositioning is done in response to an interaction between the operator and a switch or pushbutton. The operator first presses certain keys to release individual brakes and make it possible to move the respective carrier.

This type of operation has disadvantages. It may be necessary, particularly for more complex stands having a variety of medical devices (e.g., also monitors, lights), to first look for the corresponding switch, which can waste time and be irritating.

The European patent specification EP 2 455 053 B1 also notes this problem and proposes, as a solution, informing the operator through feedback whether the desired/correct brake of a stand was applied by means of the corresponding pushbutton/switch. It is also proposed that a time delay be provided for the system controller in response to an operator input. In the event of faulty operation, the operator still has time to correct the error and operate the correct switch.

An arm support device is known from JP 2009/291363 that has an arm table, a multi-point articulated arm having a variety of joints for carrying the arm table in a movable fashion, a plurality of springs to keep the joints in their respective positions, a plurality of powder brakes for controlling the braking torque for braking a movement of the joints, a plurality of encoders for detecting the operations performed in each of the joints, a 6-axis torque sensor for detecting the force and the torque that is applied to the arm table, and a control part for controlling the respective braking energy of the powder brakes, based upon a mode specified by a foot switch and upon the detection values of the 6-axis torque sensor, as well as the encoders. Releasing the powder brakes is only possible by pressing the foot switch.

BRIEF SUMMARY

The object of the present disclosure is to provide a device—in particular, a stand device having a braking device—by means of which an operator may move a medical device in a simple and intuitive manner, whether by purely manual means or with the support of a motor. In particular, the object is also to provide a stand device where individual carriers or support arms can be moved around in an operating room in a particularly simple or flexible manner, particularly without requiring much attention from the operator, thanks to a braking device that can easily be adjusted. The object may also be seen as providing a method by means of which the stand device may be moved or repositioned in an uncomplicated or intuitive manner.

This object is achieved by a stand device for arranging in an operating room and for locally moving a medical device, comprising at least one movably mounted support arm and a braking device having at least one brake that is configured to adjust a degree of freedom of movement of the at least one support arm and/or the medical device relative to the supporting device, wherein the stand device further comprises:

a control device connected to the braking device and at least one sensor device connected to the control device, the sensor device being configured to detect an external force acting on or applied to the stand device and/or a movement caused by the external force and, optionally, also the movement of the at least one support arm caused by the external force—in particular, a movement relative to the supporting device—and configured to output a corresponding measured value to the control device, wherein the control device is configured to control the braking device as a function of the measured value—in particular, to release it—and adjust the degree of freedom of movement.

This allows the stand or the medical device to be moved to a certain position intuitively and without much effort, be it by surgical staff or by a surgeon—in particular, also in a simple manner during an operation (frequently repeated repositioning). The braking device is therefore only released when force is applied to the stand device. A pushbutton or switch for releasing a brake does not need to be operated. No special knowledge about the position of any pushbuttons or switches is necessary. Rather, the redundancy of switches or keys/pushbuttons can be avoided. Similarly, no key needs to be operated to apply the brake after successfully moving the stand device. It is also not necessary to continuously press and hold any switches or keys during repositioning. An operator no longer needs to even wonder what switches are arranged on which points of the stand. Rather, to reposition the stand, it is enough, for example, to apply pressure to a side portion of a support arm or operate a control panel that is easily accessible to the operator anyway. A standard rail of a supply unit, for example, may also serve as a contact point for detecting an external force.

The detection of a movement may optionally include the detection of a translational and/or rotational movement. The sensor device may, for example, be an incremental encoder or include an incremental encoder, whether it is for an angle and/or for a straight path.

The degree of freedom of movement may also be adjusted by easing off a brake, but not completely releasing it. This is advantageous, particularly with regard to emergency running properties or the safety and flexibility during an operation. In particular, a brake that does not block the medical device, but only holds it in place with, for example, a braking torque of 70 Nm, may be eased off or released or locked/fully applied again with regard to a specific braking torque. A braking device that does not block, but provides only a braking torque that is surmountable in an emergency, is very practical, particularly for an attending physician. A brake may also be eased off at a threshold value that can be predefined, e.g., 30 Nm, or 50 Nm—in particular, in such a way that a "released" or eased off braking device still provides a minimum braking torque in, for example, the range of 10 Nm or 20 Nm.

Releasing the braking device may also include an easing off of the braking device during which a minimum braking torque or a minimum braking force is still maintained. The releasing may also be done on a time-related basis—in particular, as a function of an increase of force or torque that can be predefined. This also makes it possible to evaluate whether an external force was only caused by, for example, someone accidentally bumping into the stand device.

The stand device can be responsive to force and/or movement—in particular, with regard to the external force applied to the stand device or the movement caused by it. The stand device can also be responsive to position, i.e., have a certain degree of freedom of movement as a function of a certain position. Accordingly, the control device is configured to adjust the degree of freedom of movement of the stand device as a function of a force, a movement, a position, and/or a time. The control device may also have a clock or a timer.

The stand device may have a support system including a supporting device for the stationary positioning of the stand device in the operating room, wherein it is possible to movably mount the at least one support arm in a bearing and/or joint relative to the supporting device. The at least one support arm is movable within a radius of action as a function of a degree of freedom of movement of the support system. The degree or degrees of freedom of movement, and thus the radius of action, may, for example, be defined by the type and number of bearings or joints. The stand device may be operated and moved from different contact points. The stand device may be moved from all or any of the contact points on the stand device, be it on the medical device or on one of the support arms. It is not necessary to look for and operate any control button arranged at a single position. This therefore makes "blind" operation and positioning possible, i.e., operation that requires hardly any attention from the operator, which, in particular, provides advantages in connection with difficult or highly risky operations. A surgeon can concentrate better on the actual act of surgery.

In other words, the stand device is configured to adjust a degree of freedom of movement in response to an operation performed by the operator, i.e., in response to an external force. Preferably, the stand device is configured to only adjust the degree of freedom of movement as a function of force and/or movement values of the at least one sensor device. Preferably, the stand device may be braked or blocked or detached automatically, i.e., solely as a function of a force applied by the operator.

The detection of an external force may also include the detection of a movement—in particular, because, in the case of a fixed device, an externally induced movement (at least a relative movement that was just measurable) requires an external force. Likewise, the detection a movement may also include the detection of a force. The detection of an external force may also be done by detecting a torque. The detection of a force may alternatively or additionally be done by detecting an impulse. The control device is preferably configured to at least gradually release and/or at least gradually apply the at least one brake as a function of an external impulse or an impulse change. The evaluation of an impulse or an impulse change can facilitate the positioning of the medical device as a function of or in response to a changing operation by an operator.

The braking may, for example, be done in a pneumatic, electromagnetic, and/or frictional (mechanical) manner—in particular, selectively in individual joints or bearings.

A stand device is preferably to be understood as a device for holding, fixing in place, and/or moving at least one medical device that can be firmly mounted or positioned on a wall (in a wall mount) or a ceiling or on the floor of an operating room or any other room for medical purposes, e.g., a ceiling stand. The stand device is then not completely freely movable in the operating room, but may only be moved within a certain radius of action—in particular, relative to an attachment point or mounting point arranged on a ceiling or wall of the operating room. The stand device does not necessarily include a medical device, but may also be formed only by a support system. The stand device may be designed as a ceiling supply unit mounted on a ceiling and have one or more supply units that are mounted and may be positioned on one or two support arms. The stand device may also be designed as a monitor support. The stand device may also be designed as a so-called spring arm installed, in particular, on a wall and, for example, have a light. The stand device may also be designed as a so-called central axis mounted, in particular, on a ceiling and have a plurality of support systems, each having at least one carrier on which, for example, a monitor or a light is mounted. The stand device preferably has at least two support arms on which at least one brake of the braking device is provided.

It should be pointed out that the scope of application "in the operating room" is only given by way of example and that the stand device is also suitable, for example, in the context of intensive care, diagnostic devices, or—last but not least—ambulances or rescue vehicles.

The stand device does not necessarily have to be firmly mounted on a wall or ceiling, but may also be mounted on a mobile substructure. The mobile substructure may be positioned in a stationary manner in the room by means of, for example, brakes. In other words, the supporting device may be a mounting device for mounting on a wall or ceiling (e.g., a ceiling flange) on the one hand, or a mobile substructure or a foot or floor support on the other. The mobile substructure may then preferably be fixed or parked in such a way that a force exerted on one of the support arms does not cause the supporting device to move relative to the floor. The mobile substructure then preferably has rollers that interact with brakes, and optionally also with drives. The supporting device may, for example, be formed by a flange or some other interface with which the support system may be mounted on a ceiling that is at least approximately horizontal or a wall that is at least approximately vertically oriented.

Preferably, a medical device is to be understood as a supply unit by means of which the means for caring for a patient and/or instruments for a surgeon and/or light, clean air, or other media required in the operating room can be provided. The medical device preferably has some kind of control panel and/or some kind of display device for graphically displaying, for example, patient data. The medical device may optionally also be provided by a monitor or any other terminal device.

Preferably, a support arm is to be understood as a boom or carrier that extends in a certain direction and can ensure the desired radius of action for the different desired positions of the medical device—in particular, through a rotary movement about a swivel joint. The support arm may also be a telescopic device having an (additional) degree of freedom of movement in the translatory direction along the longitudinal axis of the support arm. The support arm does not necessarily hold a medical device, but may also be arranged between individual support arms as one of several booms. In many cases, the stand device has one or two support arms/booms.

Preferably, a braking device is to be understood as a device that is configured to define, whether it is to "freeze" or fix or release, at least one degree of freedom of movement—preferably several—and, optionally, all degrees of freedom of movement of the stand device or the medical device. The degrees of freedom may be defined on a time-related basis—that is to say, for example, releasing a brake for a period of, for example, 5 sec. The braking device may, for example, comprise at least one brake that can perform a function in the sense of a parking brake.

Preferably, an "external force" is to be understood as a force that is externally exerted by an operator on the system. An external force does not include, for example, inertial forces. An external force may also not be provided by forces exerted by any motors or drives of the system. Rather, the external force is to be understood as a force that is applied completely separately from the system.

The degree of freedom of movement of the support system or the medical device may include several degrees of freedom—that is to say, for example, translatory and/or rotational degrees of freedom in several planes or about several axes. It is not possible to only autonomously release a brake in response to an external force. Rather, the position of the support arm relative to the supporting device or relative to an additional support arm, for example, may also be determined according to other criteria—in particular, starting from a moment at which a user no longer exerts any force on the support arm. In other words, the stand device may also be designed to be self-positioning. The stand device can position itself autonomously.

According to one exemplary embodiment, the control device is configured to at least gradually release or also fully apply the at least one brake as a function of the magnitude or the direction of the external force and/or the direction of the movement and/or the path of the movement. As a result, desired moving/positioning into the desired position can be done efficiently or effectively. The external force (magnitude, direction) is preferably evaluated in any case. If, however, no more external force is exerted, a movement alone of the system can be also evaluated. Such a movement is then based, for example, on mass inertia and can be stopped, or at least gradually decelerated.

The control device is preferably configured to at least gradually release the braking device as a function of the external force detected by the at least one sensor device. Releasing as a function of the external force enables autonomous positioning or self-adjustment of the stand device, without requiring an operator to press a key or to perform any particular operator input. The operator only needs to touch the stand device or medical device and exert pressure in the desired direction.

The control device is preferably configured to fully or at least gradually apply the at least one brake as a function of the movement detected by the at least one sensor device—in particular, the direction and/or the speed. The application as a function of the movement allows independent positioning in a desired position.

Preferably, the stand device comprises the medical device, wherein the medical device is, for example, arranged at one end of the support system below the support system. A specific brake of the braking device may also be associated with the medical device.

According to one exemplary embodiment, the medical device has a braking device, wherein the braking device comprises several brakes that are each arranged on a respective support arm and/or on the medical device, wherein the control device is configured to selectively adjust the braking device with respect to the at least one support arm and/or with respect to the medical device—in particular as a function of the direction of the external force. This allows the positioning to be more precise. In particular, the external force must be applied by an operator only in one direction, even if there is a variety of support arms or joints. Nevertheless, the external force may be evaluated with regard to a variety of directions, and the degree of freedom of movement may be adjusted in a manner dependent upon the direction—in particular, in conjunction with a variety of direction-sensitive force and/or motion sensors. The medical device is preferably mounted on the at least one support arm so as to be movable relative to the support arm.

According to an exemplary embodiment, the control device is configured to adjust the at least one brake as a function of a position signal detected by a position sensor device—in particular, when the stand is at a standstill, and preferably at a standstill after a predefined minimum duration. This allows, for example, automatic application of the brake(s) as soon as the stand device is held in the desired position by the operator—in particular, for a minimum duration of, for example, 1 sec or 2 sec. The predefined minimum duration is preferably in the range of 0.5 to 3 sec. The position sensor device may be provided by one of the sensor devices, e.g., in the form of a GPS or DGPS receiver or also in the form of an acceleration sensor.

According to one exemplary embodiment, the stand device has at least one manually operable functional element—in particular, a tray on which a sensor device of the at least one sensor device is arranged—in particular, at least one force sensor. The tray can be actuated in an intuitive and easily accessible manner.

According to one exemplary embodiment, the stand device comprises the medical device and has a mounting interface in which the external force can be detected, wherein the mounting interface is provided on the medical device and wherein a first functional element—in particular, in the form of a handle or bar—is fixed in the mounting interface. The mounting interface makes it possible to detect a force or a torque in a simple manner—in particular, in a variety of directions.

According to one exemplary embodiment, the stand device has an externally accessible mounting interface in which the external force can be detected and in which at least one manually operable functional element decoupled from the braking device is fixed and on which a sensor device of the at least one sensor device—in particular, at least one force sensor—is arranged in an attachment point or mounting point. The external force may be detected by means of the functional element. It has been found that the operation can be greatly simplified by dispensing with any additional elements, i.e., if a force is measured at those interfaces which an operator usually touches anyway or out of habit (without the intention of releasing a brake). An externally accessible mounting interface is accessible to an operator from the outside in such a way that an external force can be introduced to the stand device at the mounting interface.

An operation of the stand device—in particular, an application of force to the stand device—may be detected and evaluated without an operator having to operate a separate key. The operator may move the entire stand device into a desired position by applying force via the functional element (in particular, to a tray), particularly with one hand. The tray may easily be used to cause the medical device to rotate, especially since the tray makes a large lever possible. A surgeon may push the tray more or less "blindly" into the vicinity of a surgical site, so as to, for example, provide instruments immediately adjacent to a surgical site (e.g., an implant site) on the patient, e.g., above the patient's abdomen, or adjacent to the patient's hip or knee. A functional element—in particular, a mechanical, non-electronic functional element—may be attached to the stand device, by means of which the stand device can be positioned or moved without the need for operating a switch, by having the mounting interface arranged in such a way (in particular, externally accessible) that an external force can be detected in the mounting interface.

The at least one functional element may optionally be arranged on at least one support arm and/or on the medical device. Preferably, the stand device has the medical device, wherein the functional element is attached to the medical device at an attachment or mounting point.

The at least one functional element may be mounted with a certain amount of play—in particular, flexibly and/or as a function of a minimum force—and, especially, in such a way that an operator senses that an action was detected as an operator input when he operates the functional element. In other words, the at least one functional element is then movable relative to the supply unit, at least in the range of several degrees (e.g., 10-20°) or several millimeters or centimeters, and may be configured to give the operator haptic feedback in particular. The at least one functional element may also be mounted so as to be movable with respect to the stand device.

A functional element decoupled from the braking device is preferably to be understood as a device that, considered individually, is not functionally connected to the braking device. In other words: The functional element performs a function other than actuating the braking device. The functional element is preferably a device that can be gripped manually, e.g., a handle or a bar or a tray for the placement of instruments, for example. Preferably, the functional element is arranged on the stand device in such a way that an operator can easily reach it in a standing or sitting position. The functional element may, for example, be arranged on a lower side or in the lower region of the medical device.

According to one exemplary embodiment, the stand device comprises the medical device, wherein the mounting interface is provided on the medical device, and wherein a first functional element, particularly in the form of a handle or bar, is fixed in the mounting interface. By detecting the force or movement on a functional element that is already known to the operator anyway in terms of its position and accessibility, the stand device can be moved particularly simply and intuitively. A second functional element is preferably attached to the first functional element—in particular, in the form of a tray. With this arrangement, a force may optionally be applied to the first or second functional element. This increases the flexibility during operation or the ergonomics, particularly in conjunction with specific postures and positions of a surgeon. The operator input for both functional elements may be done in the same manner and evaluated in the same manner, such that it is not necessary for the operator to distinguish between the functional elements.

According to one exemplary embodiment, the stand device has an operating area that is preferably visible to the operator or is marked as such and is accessible to the operator from outside and in which the external force can be introduced to the stand device. The operating area may, for example, be formed by a side section of a support arm or by a side of a/the medical device or by any free end of a support arm or a/the medical device. The operating area may also be marked as such, whether by color highlights and/or by a textured surface—in particular, for haptic recognition of the operating area (without visual contact). The operating area may, for example, be provided by a paneling part of a support arm or a medical device. Preferably, no functional element is arranged in the operating area.

At least one of the sensor devices may be arranged in the operating area or under the operating area. The operating area may also be backlit by means of, for example, in particular, a dimmable LED or surface lighting that preferably shines comparatively faintly, i.e., preferably a flood lamp, rather than a spotlight.

The operating area is preferably provided by a component of the stand device that was present anyway, e.g., a paneling part. There is preferably no pushbutton in the operating area, although a (central) pushbutton—in particular, a single button for all brakes—may also be provided. The pushbutton can easily make it possible to signal to the control device that there is no faulty operation, i.e., that, in particular, no external force was exerted on the stand device by mistake.

According to one exemplary embodiment, the at least one sensor device is configured for continuous operation, wherein a measured value of the external force or movement may be detected independently of the operating state of the stand device and may be output independently of the operating state. This ensures that the sensor device can detect an external force or movement independently of an operating state of the stand device—that is to say, for example, irrespective of whether a medical device of the stand device is operated. This makes it possible for the operator to move the stand device, even if the stand device or the medical device is not switched on or is currently not being used in the context of any surgical operation.

The at least one sensor device preferably has a source of energy and/or is coupled to an energy source independently of the control device. This ensures that the sensor device can detect an external force or movement independently of an operating state of the control device, and the control device, for example, can also wake from a standby mode to adjust a braking device in response to an external force.

According to one exemplary embodiment, the stand device has at least one drive that is connected to the control device for the motorized movement of at least one support arm, wherein the control device is configured to evaluate the movement caused by an external force as a function of the operating state of the at least one drive. This makes it possible to distinguish a movement caused by an operator from a movement caused by the drive.

According to one exemplary embodiment, the stand device is autonomously unbraked, wherein the control device is configured to fully or at least gradually release the at least one brake as a function of the external force detected by the at least one sensor device, if the magnitude of the external force increases (in particular, by a predetermined amount) or exceeds a predetermined threshold value. As a result, one or more brakes can be released automatically—in particular, at the moment when an operator exerts a force on the support arm or the medical device. The operator does not have to operate any additional pushbuttons or switches.

An "autonomously unbraked" stand device is preferably to be understood as a stand device where a mechanical or electrical switch or pushbutton does not necessarily have to be operated to release a brake of the stand device and/or move the stand device or medical device. Such a stand device may also be described as being "autonomously motion-free." Such a stand device may have an "autonomously self-releasing" or autonomously decoupling or autonomously releasing braking device. The term "autonomously" means that no further operator input is required. It is enough to apply the external force. Movement may occur in response to an external force—in particular, in the direction of the force.

According to one exemplary embodiment, the at least one sensor device is configured to detect a progression of force over time, wherein the control device is configured to gradually release the at least one brake as a function of the progression of force, depending upon the external force detected by the at least one sensor device—in particular, to release it faster when the force increases significantly and/or to apply it faster when the force decreases significantly. This allows the desired position to be approached in an intuitive manner. A change in the force applied by the operator can be evaluated, in order to adjust the brake(s).

According to one exemplary embodiment, the at least one sensor device is configured to detect a direction of force, wherein the control device is configured to release the at least one brake as a function of the direction of force detected by the at least one sensor device. As a result, those brakes that allow movement in the desired direction may be selectively released. This ensures that the medical device is moved only in a certain desired direction—for example, away from the patient.

According to one variant, the stand device is self-positioning, wherein the control device is configured to fully apply the at least one brake, or at least gradually apply it, as a function of the external force detected by the at least one sensor device, if the magnitude of the external force decreases (in particular, by a predetermined amount) or falls below a predetermined threshold value, and/or fully apply the at least one brake, or at least gradually apply it, as a function of the external force detected by the at least one sensor device, if the movement exceeds a predetermined path length or if the speed of the movement decreases (in particular, by a predetermined amount) or falls below a predetermined threshold value. As a result, a desired position can be found automatically—in particular, at the moment at which an operator no longer moves the support arm. By evaluating a movement speed, it is also possible to detect whether the operator is still moving the support arm or not, particularly if the at least one brake provides a reaction force that causes the movement of the support arm to be braked immediately if the support arm is no longer actively being moved by an operator by means of an external force.

According to one exemplary embodiment, the at least one support arm and/or the medical device is mounted in a linear bearing in a translationally movable manner and/or in a swivel joint in a pivotable manner, wherein at least one sensor device can be arranged in each respective joint or bearing.

According to one variant, the at least one support arm and/or the medical device is mounted in a translationally movable manner in a linear bearing, wherein the at least one sensor device is arranged on or in the linear bearing and configured to detect a force transmitted in the linear bearing, wherein the control device is configured to evaluate the magnitude of the force—in particular, as a function of a threshold value that can be predefined.

According to one variant, the at least one support arm is mounted in a swivel joint in a pivotable manner, wherein the at least one sensor device is arranged on the swivel joint and configured to detect a torque transmitted in the swivel joint, wherein the control device is configured to evaluate the magnitude of the torque—in particular, as a function of a threshold value that can be predefined.

According to one variant, the at least one sensor device is arranged on the at least one support arm—in particular, on a lateral (for example, at least approximately vertically oriented) surface of the support arm—and configured to detect a direction and/or a path of a movement of the support arm, wherein the control device is configured to evaluate the direction and/or the path with respect to the supporting device or at least one additional support arm. Preferably, the control device is configured to adjust the braking device as a function of the direction of the external force or movement.

Preferably, the braking device may be controlled by means of the control device in such a way that a movement of the support system in response to an application of force on one of the components of the stand device is permissible/possible.

According to one exemplary embodiment, at least one of the at least one sensor devices is a motion sensor that is configured to detect a movement with respect to absolute spatial coordinates—in particular, in all three spatial directions—especially a motion sensor from the group including a radar sensor, an acceleration sensor, an optical sensor, and a direction-finding sensor based upon terrestrial coupling.

Preferably, the stand device has a position sensor device that is connected to the control device and is configured to detect an absolute position of a (respective) support arm and/or the absolute position of the medical device. As a result, the control device may also take into account absolute position data—for example, to avoid collisions with other objects. The position sensor device may comprise a plurality of position sensors, each of which can be arranged at specific positions on the respective support arm or on the medical device. A respective position sensor may, for example, be provided in the form of a GPS sensor or DGPS sensor.

According to one exemplary embodiment, at least one sensor device of the at least one sensor device is arranged in a swivel joint of the stand device. In the swivel joint, a force or movement—in particular, the direction of a force or movement—can be detected in a very precise manner—in particular, based upon relative movements and without reference to an absolute position. The force/movement can also be detected when there is a variety of support arms—in particular, regardless of the components of the stand device to which the external force is applied.

According to one exemplary embodiment, the at least one sensor device is a force sensor from the group including pressure sensors, strain gauges, and torsion sensors. According to one variant, the force sensor may also detect a movement or a change in force (in particular, with reference to time) and be designed as an impulse sensor or as a torque sensor.

According to one variant, the stand device has at least one indicating device, which is connected to the control device, for indicating a relative movement that leads to a collision with the obstacle.

The aforementioned object is also achieved by a stand device for arranging in an operating room and for locally moving a medical device, comprising a braking device having at least one brake that is configured to adjust a degree of freedom of movement of the medical device, wherein the stand device further comprises a control device, connected to the braking device, that is configured to evaluate an external force applied to the stand device or a movement caused by the external force and configured to control the braking device and to adjust the degree of freedom of movement. This results in the previously explained advantages.

The aforementioned object is also achieved by a control device for a medical stand device—in particular, for a stand device according to the disclosure—wherein the control device is configured to evaluate an external force acting on the stand device or a movement caused by the external force and is configured to control a braking device of the stand device as a function of the force or movement—in particular, to release it—and, as a result, adjust a degree of freedom of movement of the stand device. This results in the previously explained advantages. Preferably, the control device is configured to adjust the degree of freedom of movement as a function of a position signal of a position sensor device.

The aforementioned object is also achieved by a method for automatically positioning a medical device on a stand device that can be arranged in an operating room—in particular, a stand device according to the disclosure described above—characterized by the following steps:

detecting an external force acting on or exerted on the stand device, or a movement caused by the external force, and, optionally, also the movement of the at least one support arm caused by the external force—in particular, a movement relative to the supporting device—preferably by means of at least one sensor device of the stand device;

outputting a corresponding measured value to a control device of the stand device;

evaluating the measured value by means of the control device—in particular, evaluating the magnitude and/or the direction of the external force and, optionally, also the movement (direction, magnitude, or path of the movement); and controlling a braking device of the stand device and adjusting the degree of freedom of movement of the medical device or the stand device by means of the control device as a function of the measured value—in particular, as a function of the magnitude and/or the direction of the external force and, optionally, also the direction of the movement and/or the path of the movement. This results in the previously described advantages. The controlling preferably includes releasing or additionally re-applying at least one brake of the braking device.

According to one variant, the medical device may also be positioned in an active, motorized manner—in particular, by controlling the braking device and/or a drive mechanism of the stand device—in each case by means of the control device.

According to one embodiment, the controlling of the braking device includes an at least gradual release of at least one brake of the braking device as soon as an external force is detected, or if the external force exceeds a certain threshold value for the first time or is exerted in a specific direction. During the at least gradual releasing, the degree of freedom of movement can be adjusted, depending upon the situation. As a result, it can be avoided that impacts or unintended impulses on the stand device result in the stand device no longer being braked/parked. According to one variant, at least one brake of the braking device is gradually or completely released as soon as the external force increases or exceeds a certain threshold value.

According to one embodiment, the braking device is gradually applied or applied completely as soon as the external craft is reduced or no more external force is detected, or as soon as the direction of the external force changes—in particular, starting from a change in direction as a function of a minimum threshold value, e.g., at least 30 or 45 degrees. The directional control makes it possible to react as quickly as possible to a changed operation, such that the medical device can be moved to a desired position as quickly as possible and without any detours.

According to one embodiment, the stand device is positioned in a fixed position by applying the braking device as a function of the external force detected by the at least one sensor device when the magnitude of the external force decreases (in particular, by a predetermined amount) or falls below a predetermined threshold value, and/or by applying the braking device as a function of the movement detected by the at least one sensor device if the movement exceeds a predetermined path length or if the speed of the movement decreases (in particular, by a predetermined amount) or falls below a predetermined threshold value. In this way, the stand device can be positioned in response to the stand device being released—in particular, the tray. The releasing of the stand device, i.e., no longer manually moving it (no or reduced external force), can be evaluated as a command that a desired position has been reached, or will be reached shortly.

According to one embodiment, the movement caused by an external force is evaluated as a function of an operating state of at least one drive of the stand device. As a result, at least one arm may be at least partially moved using a motor, and an operator can simultaneously position an additional support arm of the stand device.

The aforementioned object is also achieved by a method for automatically positioning a medical device on a stand device that can be arranged in an operating room, characterized by the following steps: detection of an external force acting on the stand device or a movement caused by the external force, and the controlling of a braking device of the stand device, and the adjustment of a degree of freedom of movement of the medical device or the stand device by means of the control device as a function of the measured value—in particular, as a function of the magnitude and/or the direction of the external force. This results in the previously explained advantages.

The aforementioned object is also achieved by using a control device for positioning a stand device in an operating room when locally moving a medical device mounted on the stand device—in particular, for positioning a stand device according to the disclosure—wherein the control device communicates with at least one braking device, as well as at least one sensor device configured to detect an external force acting on the stand device or a movement caused by the external force, and controls the braking device as a function of the measured value, and adjusts a degree of freedom of movement of the stand device. This kind of control makes operation easier and allows a higher degree of intuition or ergonomics.

BRIEF DESCRIPTION OF THE SEVERAL VIEWS OF THE DRAWINGS

The disclosure will be explained in greater detail in the following figures with the help of exemplary embodiments. Illustrated are.

DETAILED DESCRIPTION

In the context of the description of individual figures, reference is made to the other figures for reference numbers that are not explained explicitly.

Figure 1:
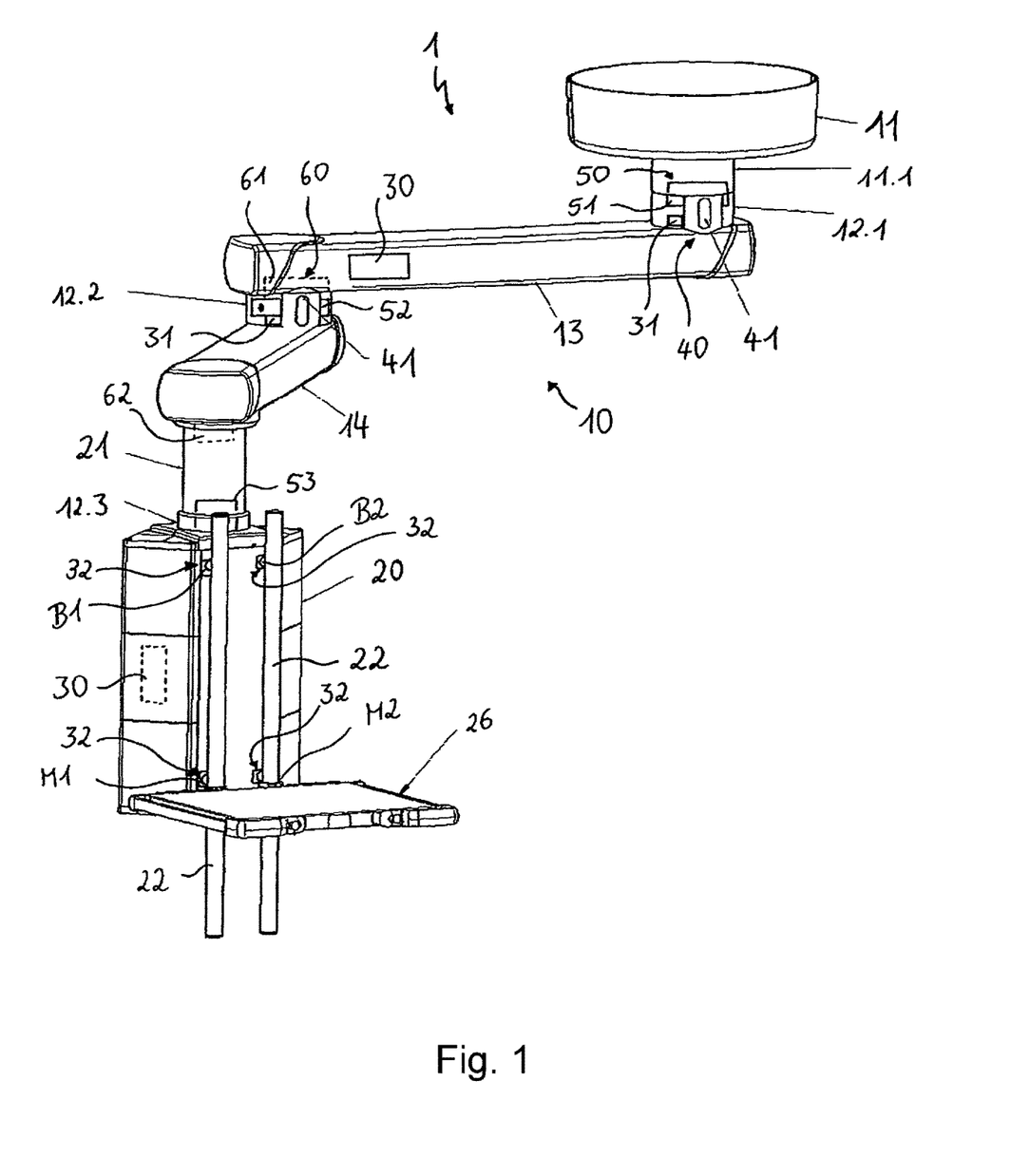
FIG. 1 schematically shows, in a perspective side view, a stand device according to an exemplary embodiment of the disclosure in conjunction with a medical device.

In FIG. 1, a ceiling stand device 1 having a support system 10 is shown that includes two support arms 13, 14. The ceiling stand device 1 may be mounted on a ceiling by means of a mounting device (ceiling flange) 11, wherein one of the support arms 13 is connected to the mounting device 11 via a support section—in particular, via a section of column 11.1. A first swivel joint 12.1 is arranged between the carrier section 11.1 and the support arm 13. A second swivel joint 12.2 is arranged on an opposite end of the support arm 13. The second swivel joint 12.2 ensures the connection to the additional support arm 14, which is connected to a third swivel joint 12.3, which ensures the connection to a medical device 20—in particular, a supply unit. The third swivel joint 12.3 may optionally also be arranged directly on the additional support arm 14. A carrier 21—in particular, a bracket pipe—which is usually rigid and permits a rotational movement, but not necessarily also a height adjustment, is arranged between the medical device 20 and the additional support arm 14. A height adjustment is preferably made by accordingly mounting the additional support arm 14 on the first support arm 13.

The medical device 20 has a functional element 22 decoupled from the braking device in the form of a handle or a bar. Furthermore, the medical device 20 has a tray 26 that functions as a "functional element."

The ceiling stand device 1 has a control device 30 that is arranged on one of the support arms in the example shown. The control device 30 may optionally also be arranged on the medical device 20, as indicated by the dotted line.

The control device 30 includes sensor devices 31 arranged on the support system 10, as well as sensor devices 32 arranged on the medical device. The sensor devices 31 on the support system 10 are preferably arranged in the joints 12.1, 12.2, 12.3. The sensor devices 32 on the medical device 20 are preferably arranged in mounting points M1, M2 and/or in attachment points B1, B2. The mounting points M1, M2 and the attachment points B1, B2 each provide an externally accessible mounting interface for the functional element 22 and the tray 26. An external force exerted on the ceiling stand device 1 may be detected, for example, at the points M1, M2, B1, B2.

Ceiling stand device 1 may optionally also have an indicating device 40 having at least one indicating element (indicator) 41. The indicating device 40 may be formed by the individual indicating elements 41 and is connected to the control device 30. The control device 30 is configured to control the indicating device 40 as a function of detected measured force values or an absolute or relative position.

The ceiling stand device 1 has a braking device 50 including at least one brake 51, 52, 53. Preferably, at least one brake is arranged at a respective interface between the support arms 13, 14 and the medical device 20 in each case. The respective brake or its position is indicated here by way of example. The braking device 50 may be formed by the individual brakes 51, 52, 53 and is connected to the control device 30.

An external force may be measured directly in the mounting and/or attachment points M1, M2, B1, B2 by means of the sensor devices 32, regardless of the point of the tray 26 or functional element 22 that the operator touches. The sensor devices 31, 32 may be configured to also measure other relative or absolute values—for example, a movement or an impulse.

The control device 30 is configured to at least release at least one of the brakes 51, 52, 53 in response to an external force—in particular, also in response to an external force having a predetermined minimum magnitude or a predetermined direction or a predetermined directional range. As a result, the ceiling stand device 1 can easily be moved (e.g., swiveled)—in particular, with one hand, or largely "blindly."

The ceiling stand device 1 also has a drive mechanism 60 including at least one drive 61, 62. Preferably, a drive is arranged at a respective interface between the support arms 13, 14 and the medical device 20 in each case. The respective drive or its position is indicated here by way of example.

The drive mechanism 60 may be formed by the individual drives 61, 62 and is connected to the control device 30.

Figure 2:
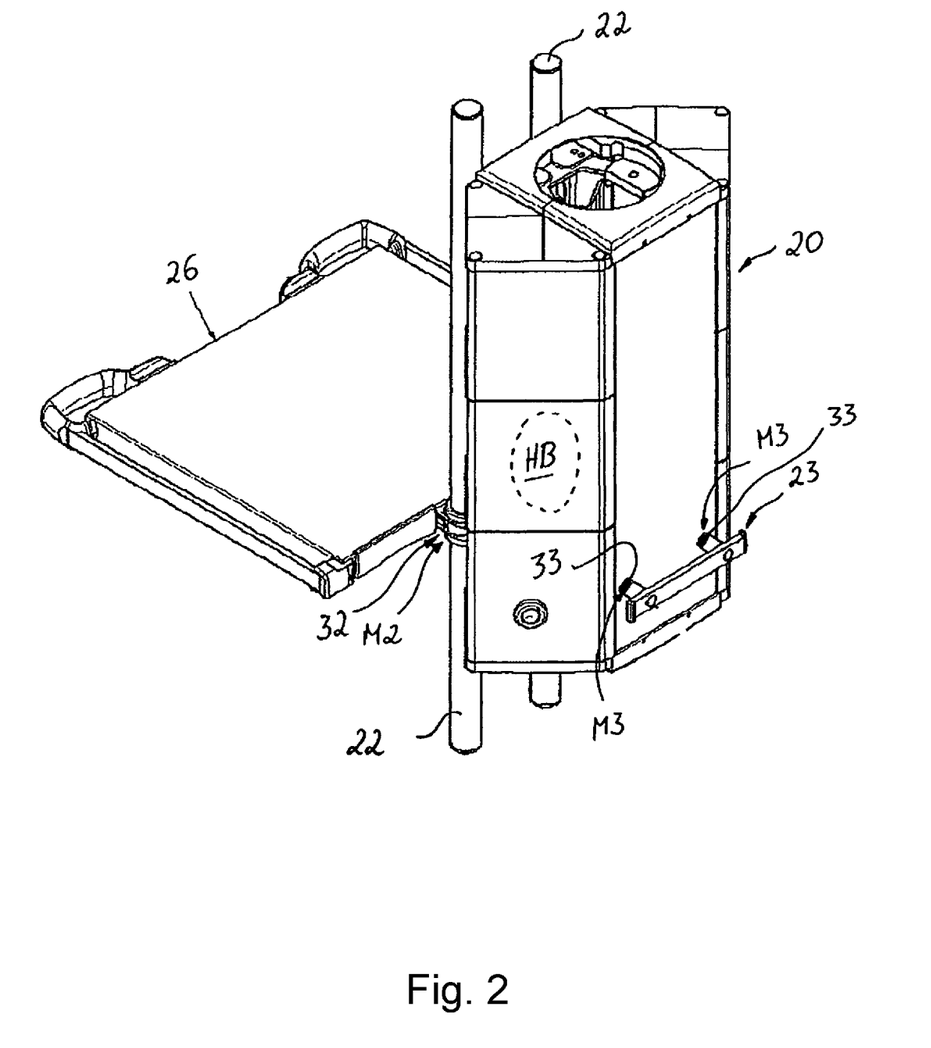
FIG. 2 schematically shows, in a perspective side view, the medical device shown in FIG. 1.

The tray 26 is shown in a further perspective in FIG. 2. The tray 26 is attached at two mounting points M2 on the functional element 22. The sensor devices 32 may be provided at the mounting interface between the functional element 22 and the tray 26 and/or at the mounting interface between the functional element 22 and the housing of the medical device 20.

Furthermore, a standard rail 23 is shown, which is attached to the supply unit in a further (third) set of mounting points M3, wherein sensors 33 (shown only schematically) may also be provided at these mounting interfaces. In addition, an operating area—in particular, haptic operating area HB—is schematically indicated, in which an operator input can be made. The operating area HB may also be arranged at other, if applicable, additional areas of the stand device—in particular, with regard to good accessibility, depending upon the application.

Figure 3:
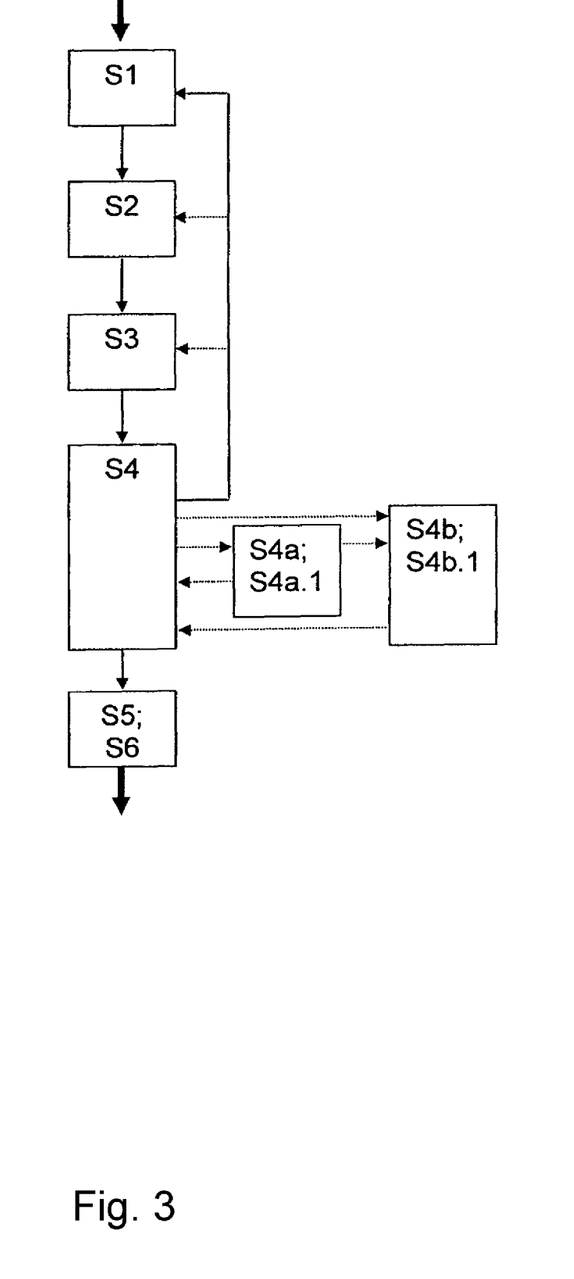
FIG. 3 schematically shows procedural steps of a method according to individual embodiments of the disclosure.

In FIG. 3, individual steps of the method for positioning the medical device are shown. The process is initiated when an external force is detected (in particular, its magnitude and/or direction) (step S1). In a second step S2, at least one measured value of the external force is output. The measured value is evaluated in a third step S3. In a fourth step S4, a braking device is controlled—in particular, at least one brake is at least gradually released or also at least gradually applied again, to adjust a degree of freedom of movement. Step S4 may include a step S4a (releasing at least one brake)—in particular, gradually releasing it (step S4a.1). Step S4 may also include a step S4b (applying at least one brake)—in particular, gradually applying it (step S4b.1). Steps S1 through S4 can be performed iteratively, be it completely or in partial steps. In a step S5, a signal/indication may be output to an operator—in particular, by means of an indicating device. Furthermore, at least one of the drives may be controlled in a step S6. Steps S5 and S6 may be performed in parallel with any of the steps S1 through S4, or also after step S4.

LIST OF REFERENCE NUMBERS 1 stand device—in particular, a ceiling stand device
10 support system
11 mounting device—in particular, a ceiling flange or floor support
11.1 carrier section—in particular, a section of column
12.1 (first) swivel joint
12.2 second swivel joint
12.3 third swivel joint
13 (first) support arm
14 second support arm
20 medical device—in particular, a supply unit
21 carrier—in particular, a bracket pipe
22 functional element decoupled from the braking device—in particular, a handle or bar
23 functional element—in particular, a standard rail
26 tray—in particular, functioning as a functional element
30 control device
31 sensor device on the support system
32 sensor device on the medical device
33 sensor device—in particular, on/in the mounting interface
40 indicating device
41 indicating element (indicator)
50 braking device
51 (first) brake
52 second brake
53 third brake
60 drive mechanism
61 (first) drive—in particular, a rotary drive
62 second drive—in particular, a rotary drive
B1 (first) attachment point
B2 second attachment point
HB operating area—in particular, a haptic operating area
M1 (first) mounting point
M2 second mounting point
M3 third mounting point
S1 first step: detecting an external force
S2 second step: outputting a measured value
S3 third step: evaluating the measured value
S4 fourth step: controlling a braking device—in particular, at least gradually releasing a brake, to adjust a degree of freedom of movement
S4a releasing a brake
S4a.1 gradual release
S4b applying a brake
S4b.1 gradual application
S5 outputting a signal/indication to an operator
S6 triggering of at least one drive The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A stand device for arranging in an operating room and for locally moving a medical device, comprising:
at least one movably mounted support arm;
a braking device having at least one brake that is configured to adjust a degree of freedom of movement of the at least one support arm and/or the medical device relative to a supporting device;
a control device connected to the braking device; and
at least one sensor device connected to the control device, the at least one sensor device being configured to detect an external force acting on the stand device or a movement caused by the external force and configured to output a corresponding measured value to the control device, wherein the control device is configured to control the braking device as a function of the measured value, the controlling including completely releasing the braking device when the external force exceeds a certain threshold value and reactivating the braking device when the external force reduces to, or less than, the certain threshold value, as a function of the measured value autonomously and without operating an additional switch based only on the external force acting on the stand device, the complete releasing causing adjustment of the degree of freedom of movement of the at least one support arm and/or the medical device relative to the supporting device.

2. The stand device according to claim 1, wherein the stand device has at least one manually operable functional element on which the at least one sensor device of the control device is arranged.

3. The stand device according to claim 1, wherein the stand device comprises the medical device and has a mounting interface in which the external force can be detected, wherein the mounting interface is provided on the medical device, and wherein a first functional element is fixed in the mounting interface.

4. The stand device according to claim 1, wherein the stand device has an operating area that is accessible from an outside and in which the external force can be introduced to the stand device.

5. The stand device according to claim 1, wherein the stand device has at least one drive connected to the control device for motorized movement of at least one support arm, wherein the control device is configured to evaluate the motorized movement caused by the external force as a function of an operating state of the at least one drive.

6. The stand device according to claim 1, wherein at least one sensor device of the control device is arranged in a swivel joint of the stand device.

7. The stand device according to claim 1, wherein the at least one sensor device is a force sensor.

8. A method for positioning a medical device on a stand device that can be arranged in an operating room, the method comprising:
    detecting an external force acting on the stand device or a movement caused by the external force;
    outputting a corresponding measured value to a control device of the stand device;
    evaluating the measured value by the control device, the evaluating including determining a magnitude or a direction of the external force or movement;
    controlling a braking device of the stand device as a function of the magnitude or the direction of the external force or movement, the controlling including completely releasing the braking device in response to the external force exceeding a certain threshold value for a first time, and reactivating the braking device when the external force returns to, or is less than, the certain threshold value.

9. The method according to claim 8, wherein the movement caused by an external force is evaluated as a function of an operating state of at least one drive of the stand device.

10. The stand device according to claim 1, wherein the control device communicates with the braking device and the at least one sensor device.

* * * * *